US009463159B2

(12) United States Patent
Potnis et al.

(10) Patent No.: US 9,463,159 B2
(45) Date of Patent: Oct. 11, 2016

(54) ORAL GEL FOR RELIEF OF TOOTH PAIN

(71) Applicant: Colgate-Palmolive Company, New York, NY (US)

(72) Inventors: Shashank Potnis, Thane (IN); Ravi Subramanyam, Mumbai (IN); Rajitha Nair, Mumbai (IN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/648,868

(22) PCT Filed: Mar. 7, 2013

(86) PCT No.: PCT/IN2013/000136
§ 371 (c)(1),
(2) Date: Jun. 1, 2015

(87) PCT Pub. No.: WO2014/087420
PCT Pub. Date: Jun. 12, 2014

(65) Prior Publication Data
US 2015/0313955 A1    Nov. 5, 2015

(30) Foreign Application Priority Data
Dec. 6, 2012 (IN) .......................... 3760/DEL/2012

(51) Int. Cl.
A61K 36/00    (2006.01)
A61K 9/00    (2006.01)
A61Q 11/00    (2006.01)
A61K 47/34    (2006.01)
A61K 31/125    (2006.01)
A61K 36/61    (2006.01)
A61K 31/085    (2006.01)
A61K 8/34    (2006.01)
A61K 8/35    (2006.01)
A61K 8/92    (2006.01)
A61K 8/04    (2006.01)

(52) U.S. Cl.
CPC ............ *A61K 9/0053* (2013.01); *A61K 8/042* (2013.01); *A61K 8/34* (2013.01); *A61K 8/347* (2013.01); *A61K 8/35* (2013.01); *A61K 8/922* (2013.01); *A61K 31/085* (2013.01); *A61K 31/125* (2013.01); *A61K 36/61* (2013.01); *A61K 47/34* (2013.01); *A61Q 11/00* (2013.01)

(58) Field of Classification Search
None
See application file for complete search history.

(56) References Cited

U.S. PATENT DOCUMENTS 6,531,115 B1    3/2003  Singh et al.
2008/0253973 A1 * 10/2008  Tamarkin et al. ............. 424/47

FOREIGN PATENT DOCUMENTS

EP    1506771    4/2008
JP    2010-083824    4/2010
WO   WO 2006019881 A2 *  2/2006  ........... A61K 31/203
WO   WO 2014/087419    6/2014

OTHER PUBLICATIONS

Bell, ed., 1848, "Camphor A Product of the Action of Nitric Acid on Amber," Pharmaceutical A Weekly Record of Pharmacy and Allied Sciences vol. IV, p. 132.
Medline Plus Supplements, 1995. "Clove Oil," http://www.nlm.nih.gov/medlineplus/druginfo/natural/251.html.
Medline Plus Supplements, 1995, "Peppermint," http://www.nlm.nih.gov/medlineplus/druginfo/natural/705.html.
Brounstein, "Toothaches," Columbines School of Botanical Studies, retrieved in 2012 from http://www.botanicalstudies.net/herbalism/toothache.php.
India, Regional Research Laboratory (Council of Scientific & Industrial Research), 1999, "Mentha x Piperita," Indian Herbal Pharmacopoeia, vol. II, pp. 67-76.
India, Regional Research Laboratory (Council of Scientific & Industrial Research), 1999, "Syzygium aromaticum," Indian Herbal Pharmacopoeia, vol. II, pp. 146-153.
International Search Report and Written Opinion in International Application PCT/IN2013/000136, mailed Nov. 7, 2013.
Leffingwell, 2009, "Cooling Ingredients and Their Mechanisms of Action", Chapter 65, from Barel, et al. (Eds), Handbook of Cosmetic Science and Technology, 3rd ed. Informa Healthcare.
Mountain Rose Herbs, 2011, "Menthol Crystals," retrieved in 2011 from https://www.mountainroseherbs.com/products/menthol-crystals/profile.
O'Connor, "Remedies: Clove Oil for Tooth Pain," retrieved in 2012 from www.Nytimes.com.
Veitch et al., eds., 2000, "Camphor Tree," Physician's Desk Reference for Herbal Medicines, 2nd ed., p. 143.
Veitch et al., eds., 2000, "Clove," Physician's Desk Reference for Herbal Medicines, 2nd ed., pp. 195-196.
Veitch et al., eds., 2000, "Peppermint," Physician's Desk Reference for Herbal Medicines, 2nd ed., p. 580-581.
Wikipedia, 2011, "Camphor," retrieved in 2011 from www.wikipedia.com.
Wikipedia, 2011, "Menthol," retrieved in 2011 from www.wikipedia.com.
Wikipedia, 2011, "Oil of Cloves," retrieved in 2011 from www.wikipedia.com.

* cited by examiner

*Primary Examiner* — Qiuwen Mi

(57) ABSTRACT

Disclosed herein are orally acceptable topical analgesic gels comprising a mixture of analgesic oils comprising (a) clove oil and/or eugenol, (b) a cooling agent, and (c) camphor; in an orally acceptable gel base, the gel base providing controlled release of the mixture of analgesic oils following application to a tooth; together with methods of making and using the same.

17 Claims, No Drawings

ORAL GEL FOR RELIEF OF TOOTH PAIN

CROSS-REFERENCE TO RELATED APPLICATIONS

This application is a U.S. national stage application under 35 U.S.C. §371 of PCT Application No. PCT/IN2013/0000136, filed Mar. 7, 2013, which claims priority to Indian Application No. 3760/DEL/2012, filed Dec. 6, 2012, the entireties of each are incorporated herein by reference.

BACKGROUND

Tooth pain is most often caused by structural damage to the tooth, wherein the nerves of the tooth, which are normally well protected by dentin and enamel, are exposed to external stimuli, for example as a result of caries, a cracked tooth, an exposed tooth root, or erosion of the enamel, as well as by gum disease, abscess, or impaction. The severity of a toothache can range from chronic and mild to sharp and excruciating. The pain may be aggravated by chewing or by cold or heat. The patient may not be able to identify the cause of the pain without a dental examination. Current symptomatic treatments include pharmaceutical analgesics—non-steroidal anti-inflammatory agents such as such as aspirin, ibuprofen, or acetaminophen, topical gel anesthetics containing lidocaine or benzocaine, and/or narcotics such as codeine—but these pharmaceuticals each have their own limitations, in that they may not be available without a prescription, may not have an immediate effect, and/or may have undesirable side effects. Home remedies may provide a brief respite from the pain, but do not remain for extended periods on the tooth and typically do not provide controlled delivery of actives or sustained pain relief.

There is a need for improved methods of treating tooth pain, which address the various types of pain, for example pain from cavities as well as from dental hypersensitivity, and which provide immediate and sustained relief from the pain.

SUMMARY

The invention provides, in a first aspect, a novel topical "leave on" gel formulation that permits sustained delivery of pain-relieving herbal extracts to the affected tooth.

The orally acceptable analgesic "leave-on" gel formulation of the invention comprises a mixture of analgesic oils comprising (a) clove oil and/or eugenol, (b) a cooling agent, e.g., selected from menthol, peppermint oil, menthyl esters, menthoxyalkanols, and p-menthane carboxamides (e.g., N-ethyl-p-menthane-3-carboxamide), and mixtures thereof; and (c) camphor, in an orally acceptable gel base, the gel base providing a sustained release of the mixture of analgesic oils following application. In one embodiment, the gel base comprises a. poly(acrylic acid), e.g., carbomer homopolymer type B, e.g., Carbopol®974P NF;
b. propylene glycol;
c. nonionic surfactant selected from poloxamers, polysorbates, and mixtures thereof;
d. neutralizing base, e.g., sodium hydroxide;
e. water; and
f. optionally sweeteners, flavorings, and/or preservatives.

In other aspects, the invention provides methods of making such formulations and of using such formulations to alleviate tooth pain. It has surprisingly been discovered that these oils are more effective as analgesics in combination with one another, perhaps because they affect different receptors. Formulation presents some challenges, as the oral cavity is essentially an aqueous environment, and the analgesic oils are only poorly soluble in water, but the structured formulations provided give stable formulations as well as effective and sustained release of the analgesic oils upon application.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used herein, the term "effective amount" means the quantity of analgesic oils required to provide relief of tooth pain. Tooth pain may be a result of caries, a cracked tooth, an exposed tooth root, or erosion of the enamel, as well as by gum disease, abscess, impaction or dentinal hypersensitivity.

The invention provides in a first embodiment, an orally acceptable topical analgesic gel (Formulation 1) comprising an orally acceptable topical analgesic gel comprising a mixture of analgesic oils comprising (a) clove oil and/or eugenol, (b) a cooling agent, and (c) camphor; in an orally acceptable gel base, the gel base providing a sustained release of the mixture of analgesic oils following application to a tooth.

For example, the invention provides e.g., 1.1. Formulation 1 wherein the gel base provides sustained release of the analgesic herbal oils for a period of at least five minutes, e.g. at least 10 minutes, e.g., at least 20 minutes following application of the formulation to a tooth.

1.2. Formulation 1 or 1.1 wherein the mixture of analgesic oils comprises 1-10% by weight of the formulation, e.g., about 5%.

1.3. Any of the preceding formulations wherein the ratio of (a) to (b) to (c) is 70-100:5-15:5-15, e.g., about 8:1:1 to about 10:1:1.

1.4. Any of the preceding formulations wherein the mixture of analgesic oils comprises eugenol or clove oil:menthol:camphor in a ratio of 70-100:5-15:5-15, e.g., about 8:1:1 to about 10:1:1.

1.5. Any of the preceding formulations wherein the cooling agent is a TRMP8 thermoreceptor agonist, e.g., selected from peppermint oil, menthol, menthoxyalkanols (e.g., 3-(1-menthoxy)-2-methylpropane-1,2-diol, 3-(1-menthoxy)ethanol, 3-(1-menthoxy)propan-1-ol, and 3-(1-menthoxy)butan-1-ol), menthyl esters (e.g., menthyl lactate and menthyl 3-hydroxybutarate), and p-menthane 3-carboxamides (e.g., N-ethyl-p-menthane-3-carboxamide (WS-3), (1R,2S,5R)—N-(4-methoxyphenyl)-p-menthanecarboxamide (WS-12), (2S,5R)—N-[4-(2-Amino-2-oxoethyl)phenyl]-p-menthane-carboxamide, N-cyclopropyl-5-methyl-2-isopropylcyclohexanecarbonecarboxamide, ethyl 3-(p-menthane-3-carboxamido)acetate (WS-5), (1R,2S,5R)—N-(4-Methoxyphenyl)-p-menthanecarboxamide (WS-12), N-ethyl-2,2-diisopropylbutanamide (WS-27), N-cyclopropyl-5-methyl-2-isopropylcyclohexanecarboxamide, N-(1,1-Dimethyl-2-hydroxyethyl)-2,2-diethylbutanamide (WS-116), N-(4-cyanomethylphenyl)-p-menthanecarboxamide, and N-(2-(pyridin-2-yl)ethyl)-3-p-menthanecarboxamide; for example N-ethyl-p-menthane-3-carboxamide), and mixtures thereof.

1.6. Any of the preceding formulations wherein the cooling agent is menthol.

1.7. Any of the preceding formulations wherein the gel base comprises an anionic polymer, e.g., a polycarboxylate, e.g., selected from poly(acrylic acid)(optionally cross-linked, e.g., with polyalkenyl ethers or divinyl glycol) and optionally additionally 1:4 to 4:1 copolymers of maleic anhydride or acid with another polymerizable ethylenically unsaturated monomer (e.g., methyl vinyl ether/maleic anhydride (PVM/MA) copolymer), in free or salt form.

1.8. Any of the preceding formulations wherein the gel base comprises one or more nonionic surfactants, e.g., selected from poloxamers, polysorbates, and mixtures thereof.

1.9. Any of the preceding formulations wherein the gel base has pH 6-8, e.g., wherein the gel base is approximately pH neutral.

1.10. Any of the preceding formulations wherein the gel base further comprises one or more astringents, e.g., herbal astringents, e.g., selected from *Terminalia arjuna* and *Acacia* extracts or powders.

1.11. Any of the preceding formulations wherein the gel base further comprises a soluble potassium salt, e.g., potassium nitrate.

1.12. Any of the preceding formulations wherein the gel base further comprises a small particle occlusive agent, e.g. a small particle silica or calcium carbonate, having a $d_{50}$ of less than 5 μm, e.g., 0.5-5 μm, e.g. a small particle synthetic amorphous silica (e.g. $d_{50}$ about 3-4 μm) and/or small particle precipitated calcium carbonate (e.g., $d_{50}$ about 0.5-3 μm).

1.13. Any of the preceding formulations wherein the mixture of analgesic oils further comprises a warming agent, e.g., a TRPV1 thermoreceptor agonists, e.g., black pepper oil, ginger oil, vanilla extract, vanillyl butyl ether, capsicum tincture, or mixtures of any of these, e.g., ginger oil, pepper oil or mixtures thereof.

1.14. Any of the preceding formulations wherein the mixture of analgesic oils further comprises an anti-inflammatory herbal oil, e.g., a phenolic herbal oil, for example thymol.

1.15. Any of the preceding formulations wherein the gel base comprises sweeteners, e.g. saccharin, flavorings (in addition to the analgesic oils), and/or preservatives, e.g., sodium benzoate.

1.16. Any of the preceding formulations wherein the gel base comprises:
  a. cross-linked poly(acrylic acid), e.g., carbomer homopolymer type B, e.g., Carbopol®974P NF;
  b. propylene glycol;
  c. nonionic surfactant selected from poloxamers, polysorbates, and mixtures thereof;
  d. neutralizing base, e.g., sodium hydroxide; and
  e. water.

For example, in one aspect the invention provides Formulation 1.17, an orally acceptable topical analgesic gel according to any of the preceding formulations comprising

| | |
|---|---|
| Carbomer homopolymer type B | 1-2%, e.g. 1-1.5% |
| Propylene Glycol | 10-20%, e.g., about 15% |
| Poloxamer | 5-15%, e.g., about 9% |
| Polysorbate | 2-7%, e.g., about 5% |
| Sodium Saccharin | 0-0.5%, e.g., about 0.2% |

-continued

| | |
|---|---|
| Sodium Benzoate | 0-0.5%, e.g., about 0.2% |
| Base, e.g., NaOH | To adjust to pH 6-8 |
| Clove oil or eugenol | 3-6%, e.g., about 4-5% |
| Camphor | 0.2-0.8%, e.g., about 0.5% |
| Menthol | 0.2-0.8%, e.g., about 0.5% |
| Water | 30-75% |

In other aspects, the invention provides methods of making such formulations and of using such formulations to alleviate tooth pain.

For example, the invention provides a method of alleviating dental pain comprising administering an effective amount of a composition of any of Formulation 1, et seq. to the affected area, e.g, wherein the composition is left on the affected area following application, e.g., for at least a minute, e.g., at least 5 minutes. The invention further provides any of Formulation 1, et seq. for use in alleviating dental pain.

In another embodiment, the invention provides the use of a mixture of analgesic oils comprising (a) clove oil and/or eugenol, (b) a cooling agent (e.g., as hereinbefore described, e.g., selected from menthol, peppermint oil, menthyl esters, menthoxyalkanols, and p-menthane carboxamides (e.g., N-ethyl-p-menthane-3-carboxamide), and mixtures thereof); and (c) camphor, in the manufacture of an orally acceptable topical analgesic gel to alleviate dental pain.

In another embodiment, the invention provides a method of making an orally acceptable topical analgesic gel, e.g., as hereinbefore described, e.g., any of Formulation 1, et seq. the orally acceptable topical analgesic gel comprising a mixture of analgesic oils comprising (a) clove oil and/or eugenol, (b) a cooling agent, and (c) camphor; together with an orally acceptable gel base comprising a cross-linked poly(acrylic acid) polymer, nonionic surfactants, and water, the method comprising first forming a water-in-oil emulsion wherein the oil phase comprises the mixture of analgesic oils, the water phase comprises the poly(acrylic acid) polymer and water, and the nonionic surfactants facilitate the emulsion formation, then raising the pH of the emulsion thus formed to a level sufficient to ionize the carboxyl groups on the cross-linked poly(acrylic acid) polymer, thereby forming a stable gel.

In various embodiments, the invention provides compositions comprising a mixture of analgesic oils comprising (a) clove oil and/or eugenol; (b) a cooling agent, e.g., selected from peppermint oil, menthol, menthyl esters, menthoxyalkanols, and p-menthane 3-carboxamides), and mixtures thereof; and (c) camphor. These analgesic oils may be from natural sources or may be synthetic. Clove oil is extracted from the buds, leaf or stem of the clove plant, *Syzygium aromaticum*. Where clove oil is used in place of eugenol, the amount used may be adjusted, so that the amount of eugenol (typically 80-90% of the clove oil) is constant. Camphor may be extracted from plants, e.g., from laurel or rosemary, or synthetically produced, e.g., from oil of turpentine. Cooling agents are known in the art and are described, e.g., in Leffingwell, "Cooling Ingredients and Their Mechanisms of Action", Chapter 65, from Barel, et al. (Eds), *Handbook of Cosmetic Science and Technology*, 3$^{rd}$ ed. Informa Healthcare (2009), the contents of which are incorporated herein by reference. Cooling agents include natural or synthetic TRMP8 thermoreceptor agonists, for example, menthol, which is the dominant component of peppermint oil, and its various derivatives, e.g., compounds having a p-menthane (1-methyl-4-isopropyl-cyclohexyl) moiety, for example menthyl esters, menthoxyalkanols, and p-menthane 3-carboxamides. The analgesic oils may in some embodiments additionally comprise one or more warming agents, e.g., TRPV1 thermoreceptor agonists, e.g., black pepper oil, ginger oil, vanilla extract, vanillyl butyl ether, capsicum tincture, or mixtures thereof, for example in an amount of 0.1-2%, e.g., ca. 0.5% ginger oil and 0.5% black pepper oil. The analgesic oils may in some embodiments additionally comprise one or more anti-inflammatory herbal oils, e.g., selected from the phenolic herbal oils, for example thymol, for example in an amount of 0.1-2%, e.g., ca. 0.5% thymol.

The gels of the invention in various embodiments utilize anionic polymers, which tend to stick to the soft and hard surfaces of the oral cavity, and provide targeted sustained delivery of the analgesic oils. Carbomers or polyacrylates, for example the various Carbopol® products, are cross-linked poly(acrylic acid) polymers, and may in certain embodiments form the principal structurant for the gels. For example, the gel may comprise cross-linked poly(acrylic acid), e.g., carbomer homopolymer type B, for example Carbopol®974P NF. These polymers have low viscosity at low pH, permitting mixing of the various components of the gel, and formation of an emulsion or suspension of the analgesic oils, but when the pH is raised by addition of a basic material, the carboxyl moieties ionize and repel one another, causing the polymer to swell and the viscosity to increase. The oil droplets trapped in the matrix remain stably suspended in the formulation, and are then released upon application. Thus the polyacrylate component is typically added in the form of the free acid and then partially or fully neutralized with a suitable base in the final formulation to form water soluble alkali metal (e.g., potassium and sodium) or ammonium salts. The polyacrylate is provided in an amount sufficient to provide a viscous gel in the final formulation, e.g., 0.5-3%, for example 1-1.5%. The compositions of the invention may in some embodiments comprise additional polymers, for example 1:4 to 4:1 copolymers of maleic anhydride or acid with another polymerizable ethylenically unsaturated monomer (e.g., methyl vinyl ether/maleic anhydride (PVM/MA) copolymer), e.g., having a molecular weight (M.W.) of about 30,000 to about 1,000,000, most preferably about 300,000 to about 800,000. Methyl vinyl ether/maleic anhydride (PVM/MA) copolymers include the Gantrez® product line, e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The additional anionic polymers when present may be present in amounts ranging from about 0.05 to about 3% by weight. Finally, in some embodiments, the compositions comprise additional thickening agents, for example, polyvinyl pyrrolidone (PVP, e.g. Plasdone® S-630), and/or silica thickeners, which form polymeric structures or gels in aqueous media, may be present. Note that these silica thickeners are physically and functionally distinct from particulate silica abrasives often used in dentifrice formulations, as the silica thickeners are very finely divided and provide little or no abrasive action. Other thickening agents may include carboxyvinyl polymers, carrageenan, hydroxyethyl cellulose and/or water soluble salts of cellulose ethers such as sodium carboxymethyl cellulose and sodium carboxymethyl hydroxyethyl cellulose. Natural gums such as karaya, gum arabic, and gum tragacanth may also be incorporated. Colloidal magnesium aluminum silicate can also be used as a component of the thickening composition to further improve the composition's texture. In certain embodiments, thickening agents in addition to the polycarboxylate may be found in an amount of about 0.5% to about 10.0% by weight of the total composition are used.

In some embodiments, the invention comprises a small particle occlusive agent, capable of plugging the dentinal tubules and reducing sensitivity of the teeth. The small particle occlusive agent may, for example, be a small particle silica or calcium carbonate, having a $d_{50}$ of less than 5 μm, e.g., 0.5-5 μm, e.g. small particle synthetic amorphous silica ($d_{50}$ about 3-4 μm) and/or small particle precipitated calcium carbonate ($d_{50}$ about 0.5-3 μm). For example, commercially available Sorbosil AC43 silica has a $d_{50}$ of 3.95 μm. The $d_{50}$ is measured using particle size measuring techniques as known in the art. For example, particle size distribution may be measured using a Malvern Particle Size Analyzer, Model Mastersizer 2000 (or comparable model) (Malvern Instruments, Inc., Southborough, Mass.), wherein a helium-neon gas laser beam is projected through a transparent cell which contains silica, such as, for example, silica hydrogel particles suspended in an aqueous solution. Light rays which strike the particles are scattered through angles which are inversely proportional to the particle size. The photodetector arrant measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the silica hydrogel, for example. It will be understood that other methods of measuring particle size are known in the art, and based on the disclosure set forth herein, the skilled artisan will understand how to calculate median particle size, mean particle size, and/or particle size distribution of particles in the present invention.

In certain embodiments, the emulsion of the oil in the gels of the invention is facilitated by surfactants. In some embodiments, the surfactants are nonionic surfactants. Illustrative nonionic surfactants that can be used in the compositions of the invention include compounds produced by the condensation of alkylene oxide groups (generally hydrophilic) with an organic hydrophobic compound which may be aliphatic or alkylaromatic. Examples of nonionic surfactants include, but are not limited to, the poloxamers (e.g., nonionic triblock copolymers composed of a central hydrophobic chain of polyoxypropylene (poly(propylene oxide)) flanked by two hydrophilic chains of polyoxyethylene (poly(ethylene oxide)), for example commercially available under the trade names Pluronic® or Kolliphor®, e.g, poloxamer 407), polysorbates (polyethoxylated sorbitan esterified with fatty acids, for example commercially available as Alkest®, Canarcel® or Tween®, e.g. polysorbate 20) and mixtures thereof. Other nonionic surfactants which may be used include polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. The surfactant or mixtures of compatible surfactants can be present in the compositions of the present invention in an amount sufficient to permit formation of an oil-in water emulsion between (i) the water and other hydrophilic components of the gel and (ii) the analgesic oils, e.g., in about 0.1% to about 20.0%, for example about 5% to about 20% by weight of the total composition.

In some embodiments, the viscosity of the compositions of the invention is greater than about 1,000 centipoise (cPs)

and less than about 900,000 cPs, in a more specific embodiment greater than about 10,000 cP and less than about 100,000 cPs, in a more specific embodiment greater than 50,000 cPs and less than 900,000 cPs, and in an even more specific embodiment from between about 200,000 cPs to about 600,000 cPs.

The compositions of the invention may optionally comprise other components, for example humectants, e.g., propylene glycol and/or glycerin, flavoring agents (in addition to the analgesic oils), sweetening agents, e.g. sodium saccharin, preservatives, e.g. sodium benzoate, basifying agents, e.g. sodium hydroxide, and/or coloring agents.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Embodiments of the present invention are further described in the following examples. The examples are merely illustrative and do not in any way limit the scope of the invention as described and claimed.

EXAMPLES

Example 1

Gels are prepared with the following ingredients:

TABLE 1

1% Oil

| Ingredient | % w/w |
|---|---|
| Carbomer (Carbopol 974P NF) | 1% |
| Propylene glycol | 30% |
| 18% w/v NaOH solution | 1% |
| Sodium saccharin | 0.2% |
| Poloxamer 407 | 10% |
| Oil blend (clove oil:menthol:camphor 50:20:30) | 1% |
| Water | q.s. |

TABLE 2

2% Oil

| Ingredient | % w/w |
|---|---|
| Carbomer (Carbopol 974P NF) | 1% |
| Propylene glycol | 40% |
| 18% w/v NaOH solution | 1% |
| Sodium saccharin | 0.2% |
| Poloxamer 407 | 4% |
| Polysorbate 20 | 2% |
| Oil blend (clove oil:menthol:camphor 50:30:20) | 2% |
| Water | q.s. |

TABLE 3

3% Oil

| Ingredient | % w/w |
|---|---|
| Carbomer (Carbopol 974P NF) | 1% |
| Propylene glycol | 15% |
| 18% w/v NaOH solution | 0.5% |
| Sodium saccharin | 0.2% |
| Poloxamer 407 | 9% |
| Polysorbate 20 | 3% |
| Sodium benzoate | 0.2% |
| Oil blend (clove oil:menthol:camphor 50:20:30) | 3% |
| Water | q.s. |

TABLE 4

5% Oil

| Ingredient | % w/w |
|---|---|
| Carbomer (Carbopol 974P NF) | 1% |
| Propylene glycol | 15% |
| 18% w/v NaOH solution | 0.5% |
| Sodium saccharin | 0.2% |
| Poloxamer 407 | 9% |
| Polysorbate 20 | 3% |
| Sodium benzoate | 0.2% |
| Oil blend (clove oil:menthol:camphor 50:20:30) | 5% |
| Water | q.s. |

Briefly, the carbomer is dispersed in propylene glycol and water and stirred, then surfactant(s), sweetener, and preservative are premixed, added and stirred. Then the oil blend is added, and the mixture homogenized. Finally the alkali is added, which raises the pH of the mixture and causes the carboxylate groups on the carbomer to ionize, resulting in a thick gel. The above formulations with varying amounts of oil component are prepared, the properties of the formulation observed, and the formulation applied to the tooth and gum of a volunteer:

TABLE 5

| OPTIMIZATION OF OIL BLEND CONCENTRATION | |
|---|---|
| Formulation prototype | Comments |
| 1.0% Carbopol 974P NF gel with 1% oil blend | Consistency of gel is like an ointment. Warm-cool sensation observed, but with little numbing |
| 1.0% Carbopol 974P NF gel and 2% oil blend | Consistency of gel thinner, warm-cool sensation observed but with little numbing, sweetness good, some oil separation |
| 1.0% Carbopol 974P NF gel and 3% oil blend | Thick, translucent gel, good spreadability, evenness, good sweetness, warm-cool sensation, fair numbing |
| 1.0% Carbopol 974P NF gel and 5% oil blend | Thick translucent gel, good spreadability, evenness, sweetness less, instant numbing, burning sensation, noticeable cool sensation of menthol. |

While none of the formulations are completely unacceptable, the 5% blend appears stable, despite the higher oil level, and provides good delivery of effective levels of active agent.

Optimization of the Oil Blend Composition:

The 5% oil formulation described above is then varied using different oil blend compositions as follows:

TABLE 6

OPTIMIZATION OF OIL BLEND COMPOSITION

| Formulation | Comments |
|---|---|
| 1.0% Carbopol 974P NF gel and 5% Clove oil:Menthol:Camphor (50:20:30) | Thick translucent gel, good spreadability, evenness, instant numbing, burning sensation, noticeable cool sensation of menthol. |
| 1.0% Carbopol 974P NF gel and 5% Eugenol:Peppermint:Camphor (50:20:30) | Thick translucent gel, good spreadability, evenness, sweetness less, slow numbing with less burning sensation, coolness not noticeable, bitterness observed |
| 1.0% Carbopol 974P NF gel and 5% Eugenol:N-ethyl-p-menthane-3-carboxamide:Camphor (50:20:30) | Thick translucent gel, good spreadability, evenness, sweetness less, slow numbing with less burning sensation, coolness instant but not long lasting, not as good as menthol |
| 1.0% Carbopol 974P NF gel and 5% Eugenol:Menthol:Camphor (70:10:20) | Gel thickness good, appearance translucent and appealing. Good numbing with pleasant warm cool sensation, bitterness less. |
| 1.0% Carbopol 974P NF gel and 5% Eugenol:Menthol:Camphor (80:10:10) | Good gel properties, considered best overall, submitted for further evaluation. |

A larger quantity of the final formulation is prepared, along with a placebo formulation comprising 0.5% methanol, but no clove oil or camphor, as well as an additional formulation with clove oil in place of eugenol (amount of clove oil adjusted to provide an equivalent amount of eugenol), as set forth in table below. These formulations are tested in subjects, and the formulations of Option 1 and 1A are found to have good application and retention properties as well as providing excellent relief of dental pain in comparison with the placebo formulation.

TABLE 7

| Formula option | PLACEBO | OPTION-1 | OPTION-1A |
|---|---|---|---|
| Description | Placebo with 0.5% Menthol | 5% oil blend (Eugenol:Menthol:Camphor, 80:10:10) | 5.7% oil blend (Clove oil:Menthol:Camphor, 94:10:10) |
| Carbopol 974P NF | 1 | 1 | 1 |
| Propylene Glycol | 15 | 15 | 15 |
| Poloxamer 407 | 9 | 9 | 9 |
| Polysorbate 20 | 5 | 5 | 6 |
| Sodium Saccharin | 0.2 | 0.2 | 0.2 |
| Sodium Benzoate | 0.2 | 0.2 | 0.2 |
| 50% NaOH Solution | 0.6 | 0.6 | 0.56 |
| Clove oil | — | — | 4.71 |
| Eugenol | — | 4 | — |
| Camphor | — | 0.5 | 0.5 |
| Menthol | 0.5 | 0.5 | 0.5 |
| Water | 68.5 | 64 | 62.33 |
| Total | 100 | 100 | 100 |

Example 2

The compositions of the present invention can be prepared according to the following method:

1. Disperse the Carbopol 974P NF in formula quantity of propylene glycol and some portion of water.
2. Ensure even dispersion and wetting of the Carbopol in propylene glycol and water blend with the help of homogenizer.
3. Avoid very high agitation to prevent air entrapment and lump formation.
4. Add formula quantity of Poloxamer 407, Polysorbate 20, sodium saccharin and sodium benzoate to the remaining amount of water.
5. Mix all the ingredients together at low speed in the mixer.
6. Continue mixing till an even dispersion is obtained.
7. After ensuring even dispersion of both blends, add the polymer dispersion to the poloxamer dispersion in the mixer.
8. Allow mixing of both till a smooth even dispersion is obtained.
9. Add formula quantity of oil blend to the dispersion and mix for some time without vacuum.
10. Then mix at high speed under full vacuum to ensure complete emusification
11. Add formula quantity of alkali to the dispersion at high speed and full vacuum to neutralize the polymer and to get the final thick gel.

We claim:

1. An orally acceptable topical analgesic gel comprising a mixture of analgesic oils comprising (a) clove oil and/or eugenol, (b) a cooling agent, and (c) camphor, wherein the ratio of (a) to (b) to (c) is from 8:1:1 to 10:1:1; and an orally acceptable gel base,
wherein the gel base provides controlled release of the mixture of analgesic oils following application to a tooth, and wherein the gel base comprises an anionic polymer in free or salt form.

2. The analgesic gel of claim 1, wherein the gel base releases an effective amount of the analgesic oils to the tooth after 30 seconds.

3. The analgesic gel of claim 1, wherein the gel base releases an effective amount of the analgesic oils to the tooth after 60 seconds.

4. The analgesic gel of claim 1, wherein the gel base delivers an effective amount of the analgesic oils to the tooth for at least 5 minutes.

5. The analgesic gel of claim 1, wherein the gel base delivers an effective amount of the analgesic oils to the tooth for up to 120 minutes.

6. The analgesic gel of claim 1, wherein the mixture of analgesic oils comprises 1-10% by weight of the formulation.

7. The analgesic gel of claim 1, wherein the cooling agent is menthol.

8. The analgesic gel of claim 1, wherein the mixture of analgesic oils comprises clove oil:menthol:camphor in a ratio of 8:1:1 to 10:1:1.

9. The analgesic gel of claim 1, wherein the gel base comprises a crosslinked poly(acrylic acid).

10. The analgesic gel of claim 1, wherein the gel base comprises a methyl vinyl ether/maleic anhydride (PVM/MA) copolymer.

11. The analgesic gel of claim 1, wherein the gel base comprises one or more nonionic surfactants selected from poloxamers, polysorbates, and mixtures thereof.

12. The analgesic gel of claim 1, wherein the gel base has pH from 6 to 8.

13. The analgesic gel of claim 1, wherein the gel base comprises one or more astringents.

14. The analgesic gel of claim 1, wherein the mixture of analgesic oils further comprises a warming agent.

15. The analgesic gel of claim 1, wherein the mixture of analgesic oils further comprises an anti-inflammatory herbal oil.

16. A method of alleviating dental pain comprising administering an effective amount of an analgesic gel according to claim 1 to the affected area, wherein the composition is left on the affected area following application for at least a minute.

17. A method of making an orally acceptable topical analgesic gel comprising a mixture of analgesic oils comprising (a) clove oil and/or eugenol, (b) a cooling agent, and (c) camphor; and an orally acceptable gel base comprising a cross-linked poly(acrylic acid) polymer, nonionic surfactants, and water, comprising:
   a) forming a water-in-oil emulsion wherein the oil phase comprises the mixture of analgesic oils, the water phase comprises the poly(acrylic acid) polymer and water, and the nonionic surfactants facilitate the emulsion formation,
   b) raising the pH of the emulsion thus formed to a level sufficient to ionize the carboxyl groups on the cross-linked poly(acrylic acid) polymer, thereby forming a stable gel;
wherein the ratio of (a) to (b) to (c) is from 8:1:1 to 10:1:1.

* * * * *